United States Patent
Tamari

[19]

[11] Patent Number: 5,927,951
[45] Date of Patent: Jul. 27, 1999

[54] SAFETY DEVICES FOR PERISTALTIC PUMPS

[76] Inventor: Yehuda Tamari, 21 Singworth St., Oyster Bay, N.Y. 11771-3703

[21] Appl. No.: 08/831,188

[22] Filed: Apr. 2, 1997

Related U.S. Application Data

[63] Continuation-in-part of application No. 08/485,016, Jun. 7, 1995, which is a continuation-in-part of application No. 07/852,931, Mar. 13, 1992, Pat. No. 5,186,431, which is a continuation-in-part of application No. 07/683,093, Apr. 10, 1991, which is a continuation of application No. 07/410,845, Sep. 22, 1989, said application No. 07/852,931, is a continuation-in-part of application No. 07/669,641, Mar. 14, 1991, Pat. No. 5,215,450.

[51] Int. Cl.⁶ ..................................................... F04B 43/08
[52] U.S. Cl. ............................. 417/63; 417/476; 604/153
[58] Field of Search ............................. 417/63, 474, 476, 417/477.1, 307; 604/153

[56] References Cited

U.S. PATENT DOCUMENTS

| | | | |
|---|---|---|---|
| 4,515,589 | 5/1985 | Austin et al. | 604/122 |
| 4,650,471 | 3/1987 | Tamari | 604/153 |
| 4,767,289 | 8/1988 | Parrott et al. | 417/477 |
| 4,828,462 | 5/1989 | McBurnett | 417/310 |
| 5,052,900 | 10/1991 | Austin | 417/477.1 |
| 5,336,051 | 8/1994 | Tamari | 417/474 |

FOREIGN PATENT DOCUMENTS

1229425 A1   5/1986   U.S.S.R. ................................ 417/477.1

*Primary Examiner*—Timothy Thorpe
*Assistant Examiner*—Peter G. Korytnyk

[57] ABSTRACT

The present invention is a disposable combination of tubing components for use with the roller pump that limits the negative pressure said pump generates (e.g. during left ventricular venting). The device consists of pump tubing and a shunt with resistance to flow placed between the inlet and outlet of the pump tubing. The device may also incorporate interconnecting tubing and a one way valve at the pump inlet tubing. The valve decreases the likelihood of pumping air or fluid into the ventricle with accidental pump reversal. In one preferred embodiment the device is called the Better-Venterä. The pump tubing of the device collapses more readily than tubing currently being used for either venting or suction applications, thus limiting the negative pressure generated by the pump to safer levels. In addition, the maximum suction generated by the pump is further limited by recirculation of flow between the pump inlet and outlet. The recirculation acts to "break" high suction. As pump inlet pressure decreases, flow through the shunt increases to maintain the negative pressure above that possible without the recirculation line. If a higher suction is desired, the shunt tubing can be clamped. Unlike present devices, the Better-Venter™ provides additional safety in a completely contained system, without introducing air into the blood lines or releasing blood external to the circuit.

20 Claims, 5 Drawing Sheets

LV VENT PUMP

SAFETY DEVICES FOR PERISTALTIC PUMPS

CROSS-REFERENCES TO RELATED APPLICATIONS

This application is a continuation-in-part of my co-pending application U.S. Ser. No. 08/485,016 filed Jun. 7, 1995 entitled "Pressure Sensitive Devices for Extracorporeal Pumping", still pending; which is continuation-in-part of U.S. Ser. No. 07/852,931, now U.S. Pat. No. 5,186,431 filed Mar. 13, 1992 entitled "Pressure Sensitive Valves for Extracorporeal Circulation"; now, which is a continuation-in-part of U.S. Ser. No. 07/683,093 filed Apr. 10, 1991 entitled "Pressure Sensitive Valves for Extracorporeal Circulation", now abandoned, which was a continuation of U.S. Ser. No. 07/410,845, filed Sep. 22, 1989 also abandoned. The aforesaid U.S. Ser. No. 07/852,931, now U.S. Pat. No. 5,186,431 filed March 13, 1992 referred to above and entitled "Pressure Sensitive Valves for Extracorporeal Circulation" is also a continuation-in-part of U.S. Ser. No. 07/669,641, now U.S. Pat. No. 5,215,450, filed Mar. 14, 1991, entitled "Innovative Pumping System"; the disclosures of which applications are incorporated herein by reference thereto.

BACKGROUND OF THE INVENTION

1. Field of the Invention

The major application for the invention is roller pumps used for extracorporeal circuits to pump physiological fluids and peristaltic pumps for industry. The description of the invention hereinafter makes extensive use of cardiopulmonary bypass applications. This emphasis is made for description only. It should be understood that the described art is easily extended to other applications utilizing roller pumps. The invention discloses the combination of shunt, with or without a pressure loaded valve, connecting the inlet and outlet of the tubing used in peristaltic pumps, said shunt used to limit pump inlet pressure to safe levels. The resistance of the shunt (and/or valve) to flow is such that the shunt flow is low compared to pump flow when the pump tube is full but increases to a significant amount as the pump tube collapses and/or as the pressure difference between pump inlet and pump outlet increases.

2. Description of the Prior Art.

The simplicity and availability of the standard roller pump have made it the choice for dialysis and routine cardiopulmonary bypass. The standard tubing used to pump blood with the roller pump is almost always polyvinyl chloride (PVC) with a nominal size from ¼" internal diameter (ID) with a 1/16" wall, to ½" ID with a 3/32" wall. Although soft tubing (e.g. 40 to 55 Shore A) are available, tubing with a more rigid wall (e.g., 65 to 75 Shore A) are used almost exclusively. Use of thick, more rigid walled tubing results in the roller pump maintaining a constant flow independent of clinically expected changes in inlet pressure. Thus, a decrease in blood supply at the pump inlet, without a concomitant decrease in pump speed, can cause excessive suction, leading to air embolism, thrombosis and damage by the "venous" cannula to the patient's intima. Tests have shown that when starting at equilibrium using a PVC tube with ¼" ID and 1/16" wall, a 30% drop in inlet flow caused the inlet pressure to drop from 0 to −450 mmHg.

When the roller pump is used during cardiac surgery for venting the heart (e.g., left atrium, left or right ventricle) or for collecting shed blood from the chest cavity it requires the constant surveillance by a trained perfusionist to assure that excess suction does not occur. Alternatively, a suction relief valve (e.g. RLV-2100 "B" American Omni Medical Inc., Costa Mesa Calif. 92626, U.S. Pat. No. 4,758,224 and William Harvey's H-130 Overpressure Safety Valve, C. R. Bard Inc., Tewksbury, Mass. U.S. Pat. No. 4,502,502) can be placed at the pump inlet. These valves relieve suction at the pump inlet by incorporating a preloaded one way valve that introduces air into the blood. However, air introduction into the blood stream result in an annoying whistling sound and may increase hemolysis. These valves also prevent blood from being pumped into the heart by an accidental reversal of the pump rotational direction with a one way duck bill valve (e.g. Model VL614-101, Vernay Lab. Yellow Spring Ohio). However, if such eversal occurs, blood spatters out of the valve as far as 10ft, a major infectious hazard o operating room personnel.

U.S. Pat. Nos. 4,515,589, 4,767,289 and 4,650,471 describe devices to be used with the roller pump to regulate flow as a function of inlet pressure that utilize thin wall tubing (e.g. 0.375" ID with a 0.010" wall with ID/Wall= 37.5) housed inside standard thick wall tubing. One (U.S. Pat. N. 4,767,289) also incorporates a one way valve at the pump outlet to prevent accidental back flow to the patient. These devices are expensive to manufacture and therefore have not been commercially successful.

SUMMARY OF THE INVENTION

The present invention provides the benefits of prior art devices (limiting pump inlet pressure and the possibility of pumping air or fluid into the ventricle with accidental pump reversal) while avoiding their disadvantages (annoying noise, introduction of air into the blood stream, or the spattering of blood external to the circuit). Further, its advantages and uniqueness are also enhanced by providing the user with means to adjust the degree of suction the pump can generate.

Studies with various sized tubing in a roller pump indicate that before tube collapse begins due to a decrease in pump inlet pressure, a critical inlet pressure (Pc) must be reached. Tubes with a higher ID/wall ratio or a lower Shore hardness have a lower Pc. Tubes with lower Pc also have flow reduction occur over smaller changes in inlet pressure (see U.S. Pat. No. 5,215,450). But even with thin walled or soft tubing, once the pump flow reaches less than 20% of unimpeded flow, the roller pump still can generate high negative inlet pressure because large forces are required to completely collapse the circular cross section of the tubing, see FIG. 6A and 6B.

Briefly, the present invention consists of a flexible polymeric tubular member that, when placed in a roller pump, starts to collapse before pump inlet pressure reaches the maximum acceptable pump inlet pressure (e.g., nominally between −25 to −300 mmHg for venting the left ventricle). The early collapse of the pump tubing reduces pump flow, thereby limiting the suction generated. For example, the invention may utilize softer and/or thinner walled tubing that provides a 70% drop in flow when pump inlet suction is less than −200 mmHg. The high suction generated when the tube is almost completely collapsed is eliminated by a shunt tubing connecting the pump inlet to the pump outlet, said shunt "breaking" said high suction by diverting flow from the pump outlet to pump inlet. The effect of shunt flow on pump inlet pressure increases as the shunt flow increases (e.g. increasing inlet suction) and as pump flow decreases (e.g. tube collapse). In one embodiment a one way-valve in the pump inlet tubing decreases the likelihood of accidental fluid pumping into the ventricle.

The objective of the present invention is to provide a simple, safe, self-regulating device that limits the degree of suction generated by roller pumps used to withdraw blood to safe levels.

A further objective of the present invention is to limit pump inlet pressure without introducing air into the blood.

Yet another objective of the present invention is to limit the possibility of fluid being pumped into the patient or the spattering of blood external to the circuit that endangers operating room personnel and patient alike.

Another objective of the present invention is to limit pump inlet pressure without producing noise.

Another objective of the present invention is to reduce the cost of the device by innovative engineering and the use of parts used in mass production of dialysis circuits.

Another objective of the present invention is to reduce the possibility of excess pressure at the pump outlet caused by accidental obstruction of pump outlet tubing.

A further objective of the present invention is provide an open channel for venting by gravity drainage even if the pump is not running.

Another objective of the present invention is to eliminate one of the connectors used with prior art circuits by utilizing the open end of the tube at the pump inlet as the connector.

Other objectives, features and advantages of the present invention will become apparent by reference to the following detailed description of the presently preferred, but nonetheless illustrative, embodiments thereof with reference to the accompanying drawings therein:

BRIEF DESCRIPTION OF THE DRAWINGS

FIG. 5c is a schematic representation a bi-directional pre-loaded pressure valve shown in FIG. 5a incorporated into a shunt as illustrated in FIG. 2a;

DESCRIPTION OF THE PREFERRED EMBODIMENTS

Reference should now be made to the drawings wherein the same reference numerals are used throughout to designate the same or similar parts.

Figure 1:
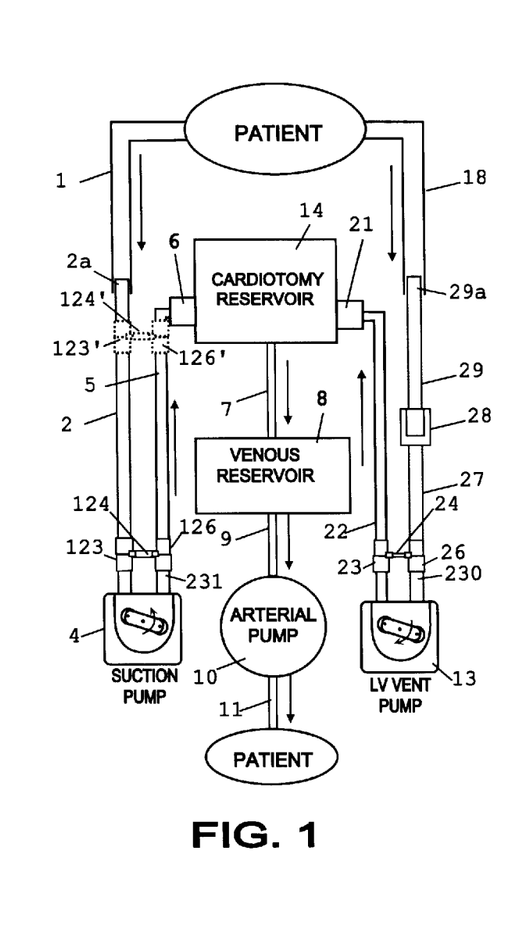
FIG. 1; is a line drawing of the pertinent components of a typical cardiopulmonary bypass circuit, illustrating two locations where the present invention can be used.

FIG. 1 illustrates a line drawing of a typical cardiopulmonary bypass with two pumps circuit pertinent to the present invention. Suction pump 4 is used to draw blood that spills into the chest cavity. Venting pump 13 is used to empty the heart. The blood of both circuits is pumped to a cardiotomy reservoir and then returned to the patient via arterial pump 10.

In the circuit with suction pump 4, a length of tubing 1 is connected at one end to a suction catheter (not shown) and is used to draw blood that spills into the chest cavity (not shown) of a patient undergoing cardiac surgery. Usually tubing 1 has a ¼" ID and is connected by the user to tubing 2 via a ¼" by ¼" polycarbonate perfusion connector (e.g. part # EC-2125, Gish Biomedical Santa Ana, Calif. 92705 not shown). The connector usually delineates the sterile patient field and the heart-lung machine. One innovation of the present invention is that the outside diameter of tube 2 fits snugly to seal inside tube 1 at 2a. For this purpose, the OD of tube 2 is preferably 0.275±0.005" allowing interference fit to seal along the inside diameter of tube 1 (ID= 0.250±0.005). For easier and more secure connection, it is advantageous to have the wall of tube 2 more rigid (e.g. Shore hardness 85A) than the wall of tube 1. In the U.S. market, the latter usually has a Shore hardness of 65±5 A. A rigid connector may also be made to form the connection between tube 1 and 2. The outlet of tube 2 forms fluid communication to the inlet of suction pump 4 and shunt tubing 124 via three way connector 123. The outlet of suction pump 4 is connected to a second three way connector 126, said three way connector forming fluid communication between one open end of shunt tubing 124, pump tubing 231 and the inlet of tube 5. Tube 5 provides a fluid path for the patient's blood being withdrawn by roller pump 4, serving as a suction pump, to cardiotomy reservoir 14. To reduce cost and priming volume, tube 5 may have a smaller diameter than the standard ¼" ID tubing used. If a smaller ID tubing 5 is used, its outlet may require adapter 6, a short ¼" ID flexible tubing, that fits the connections to a standard cardiotomy reservoir (e.g., Model # BCR3500 Baxter/Bentley Irvine Calif.). From reservoir 14 the blood usually flows to venous reservoir 8 via tube 7, pumped via tube 9 by arterial pump 10 back to the patient via tube 11. The usual gas/heat exchange device and filter used in such circuits are not shown.

Figure 2A:
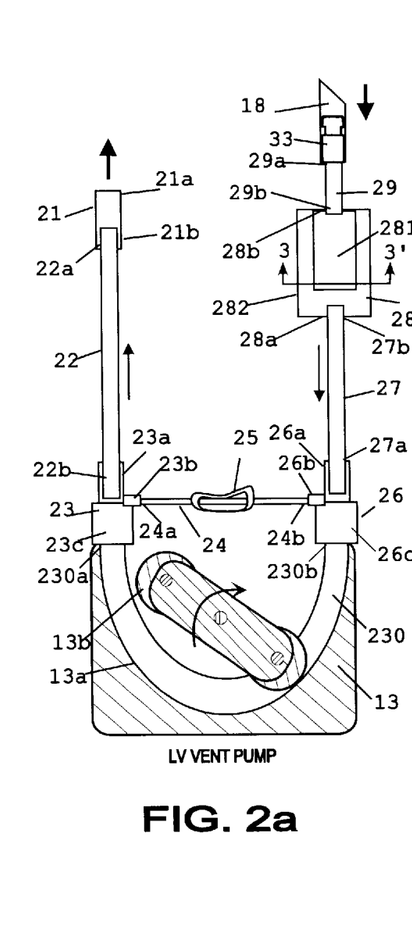
FIG. 2a is a line drawing of one preferred embodiment of the present invention using a shunt with resistance to flow.
Figure 2B:
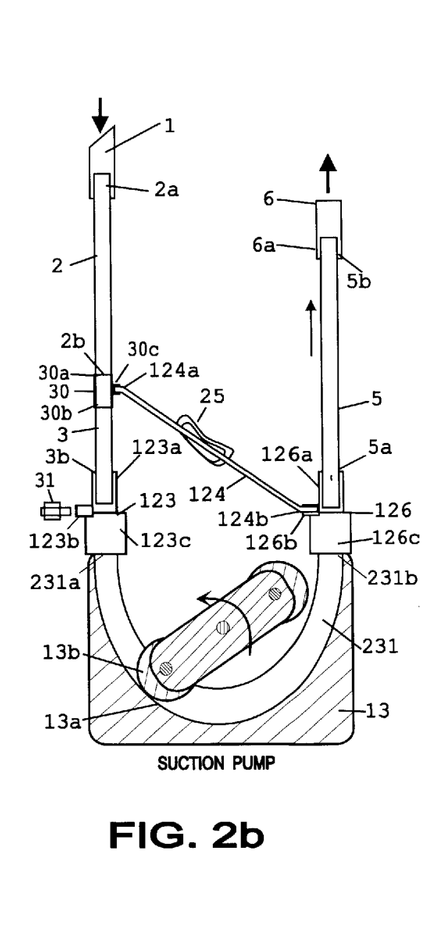
FIG. 2b is a line drawing of another preferred embodiment of the present invention using a shunt with resistance to flow.
Figure 6A:
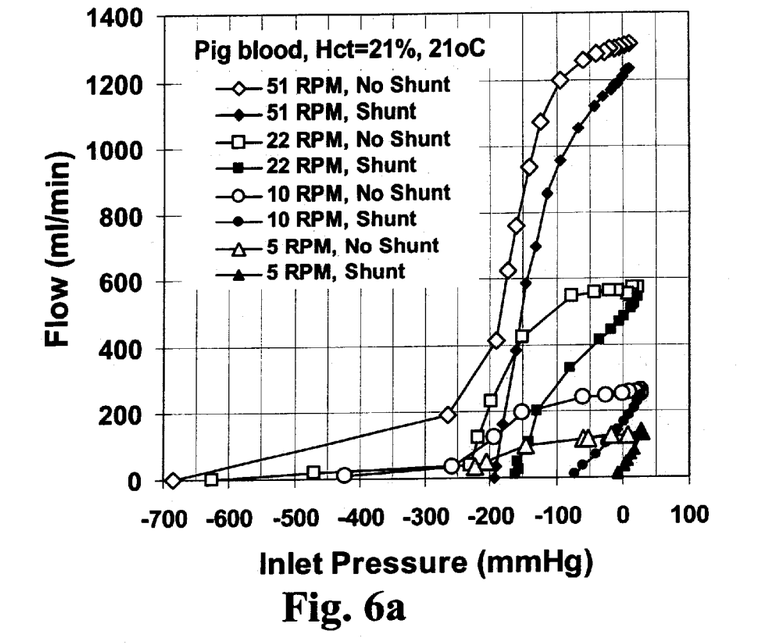
FIG. 6a illustrates typical data of pump flow as a function of pump inlet pressure for one preferred tubing of the invention.
Figure 6B:
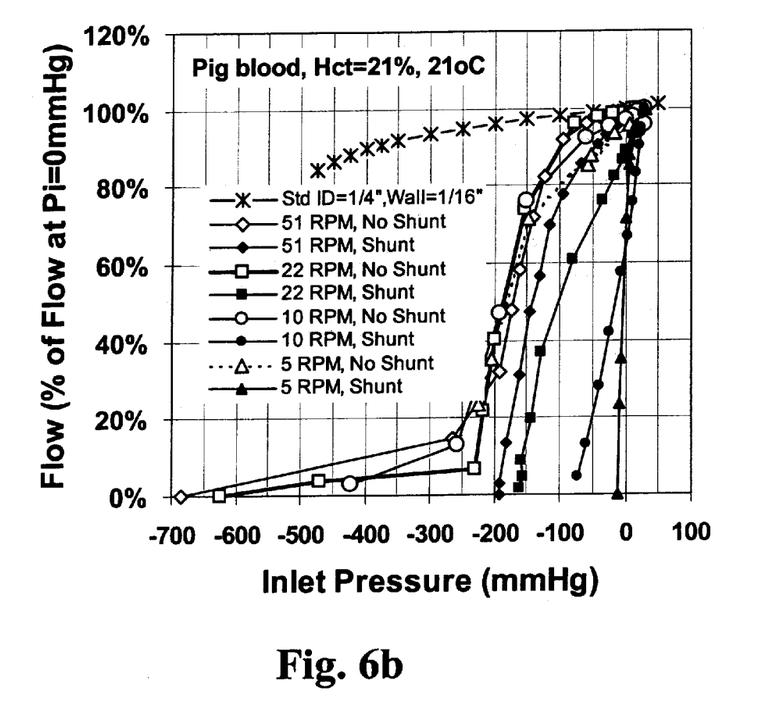
FIG. 6b illustrates the data shown in FIG. 6a comparing pump flow, expressed as a percent of nominal flow, for one of the preferred tubing for the invention to that for standard tubing.

To assure that suction pump 4 does not generate excess suction, the circuit combines properties of pump tubing 231, as illustrated in FIG. 2b and shunt tubing 124. Tube 231 preferably starts to collapse before excess negative Inlet pressure (Pin) is generated (e.g., -125>Pin>-25 mmHg). This can be achieved by using a softer tube than is generally used and/or increasing the ID/wall ratio of the tube as described in my U.S. Pat. No. 5,215,450 entitled "Innovative Pumping System for Peristaltic Pump". One preferred choice for tubing 231 is a tube with 55 Shore A wall having a nominal ID of ⅜" and wall of 1/16" (ID/wall=6). Typical pump flows possible at different pump inlet pressures obtained with this tubing placed in a 6" Stockert pump head (Sorin Biomedical, Irvine, Calif.) for different pump speeds are shown in FIG. 6a as the dashed lines. FIG. 6b expresses the flow as a percent of the flow obtained when inlet pressure is atmospheric (0 mmHg), hereinafter referred to as rated flow. FIG. 6b also compares the data taken with a tube typically used in the suction pump (¼" ID, 1/16" wall, 65 A Shore hardness, e.g., Tygon S-50-HL made by Norton Co. Akron, Ohio) to a plurality of data points obtained at different pump speed (RPM) with a shunt (solid lines) and without a shunt (dashed lines) while using the aforementioned tube 231. It is clear that with the standard tube a 10% drop in flow can result in suction greater than 400 mmHg at the pump inlet. By contrast, with tubing 231 used with the present invention, a 10% drop in flow results in a nominal suction of -100 mmHg at the pump inlet. With tubing 231, a flow reduction of over 50% is required to generate a nominal suction of -400 mmHg.

Figure 7:
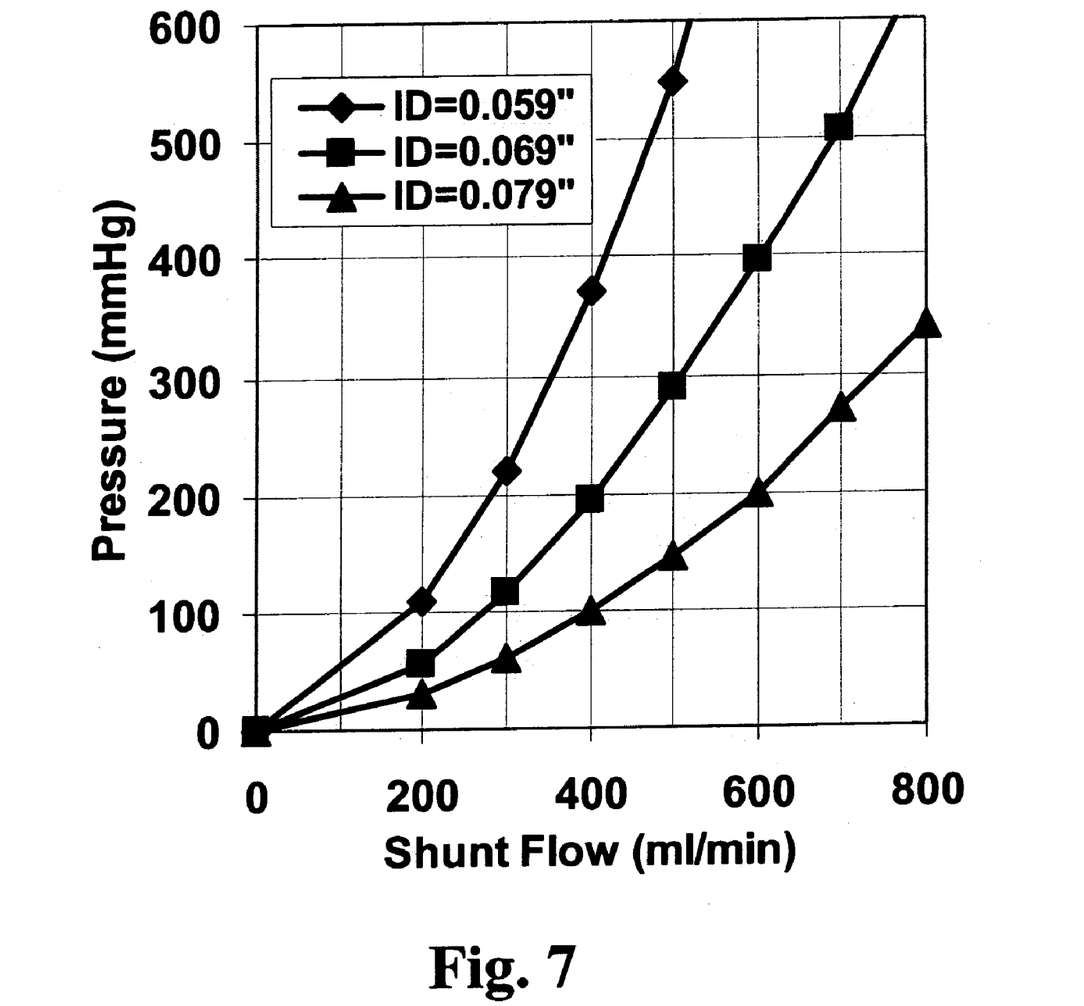
FIG. 7 illustrates data of pump outlet pressure as a function of pump flow for three different shunt resistance tubing when the pump is accidentally reversed.

Though softer tubing 231 results in significantly lower suction over a greater reduction in flow than the standard tube, it still generates high suction when the pump inlet is almost or completely obstructed. In general, such tube collapse results in less than 20% of rated flow. To limit pump inlet pressure to safer clinical levels, the invention places shunt 124 to make fluid communication between pump inlet 231a and pump outlet 231b. Shunt 124 is designed to accommodate the flow generated by pump 4 at the maximum negative pressure chosen for the setup. It is clear from the data given in FIG. 6 that the maximum shunt flow at the maximum acceptable inlet pressure should equal the flow that can be generated by the pump tubing at that maximum acceptable inlet pressure. In practice, cardiotomy reservoir 14 is nominally 50 cm above suction pump 4 and therefore the pressure at the shunt outlet (Pout) when tube 5 is filled with blood is nominally 40 mmHg. Thus, the pressure across shunt 124 equals the difference between pressure at connection 123 and connection 126. Thus, to limit the pump inlet pressure to -200 mmHg, the maximum nominal acceptable pressure across shunt 124 is 240 mmHg. Note that pump outlet pressure is further increased due to the pressure required to overcome the resistance in tube 5. If a pressure of -200 mmHg is the maximum desired inlet pressure then FIG. 6b dictates that the pump flow for the aforementioned shunt tube 124 (dashed lines) at an inlet pressure of -200 mmHg is nominally 20 to 30% of rated flow. Thus, the shunt flow, and therefore shunt dimensions, can be calculated. For example, for a rated flow of 1200 ml/min using the aforementioned properties for tube 231, and an inlet pressure of -200 mmHg, nominal shunt flow should be 400 ml/min (i.e. ⅓ of 1200). If shunt 124 is to be placed directly across pump 4, then, for the standard roller pump with 6" raceway, aesthetically and practically its length should be 5.0±1.0". FIG. 7 and Table 1 illustrate the calculated shunt flow as a function of pressure difference for a 5" long tube with three different internal diameters for blood having a viscosity 2.5 times that of water. As indicated, the shunt tube should have an ID of 0.069" to accommodate a flow of 400 ml/min at pressure of 200 mmHg. FIG. 6a and FIG. 6b illustrate the measured flow with and without such dimensioned shunt placed between pump inlet and outlet. With said shunt (solid lines) the suction generated is limited to less than -200 mmHg even at a rated flow of 1200 ml/min. Without said shunt (dashed lines) the suction at the pump inlet can be greater than -700 mmHg, which is significantly greater than the safe levels of -300 mmHg indicated from data collected with prior art devices, see Table 2. The combination of the shunt and tubing resulted in an inlet suction ranging from 0 to -190 mmHg.

It should be obvious that various combinations and permutations of length and diameter can be used for shunt 124 to achieve the same resistance, or different resistance as dictated by the desired conductance to flow, (ml/min)/mmHg. Table 1 illustrates this concept. Here, the flow through the shunt (Qshunt) is given for a 5" long shunt with IDs ranging from 0.059" to 0.079" at inlet pressures of -200 and -300 mmHg. The rated flow was then calculated as 3.33 times $Q_{shunt}$. As expected, shunt flow (and rated flow) increases either by increasing the ID of the shunt and/or accepting greater suction at the pump inlet (e.g. -300 instead of -200 mmHg).

TABLE 1

| Nominal rated blood flow (ml/min) with a 5" long shunt. | | | | |
| --- | --- | --- | --- | --- |
| | Max. inlet suction = -200 mmHg | | Max. inlet suction = -300 mmHg | |
| ID inch | $Q_{shunt}$@P = 200 | Rated flow | $Q_{shunt}$@P = 300 | Rated Flow |
| 0.059 | 260 | 867 | 330 | 1100 |
| 0.069 | 410 | 1367 | 510 | 1700 |
| 0.079 | 600 | 2000 | 750 | 2500 |

Figure 4:
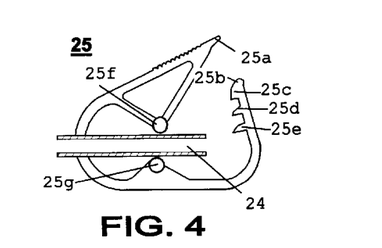
FIG. 4 is a schematic of a multi-position tubing clamp that can be used to adjust resistance to flow through the shunt shown in FIG. 2.

The maximum suction generated can also be adjusted during manufacturing by adjusting the properties of pump tubing 231. For example, increasing the wall thickness, decreasing the ID, or using a tube with higher Shore hardness would require greater suction to collapse the tube, shift the curves in FIG. 6a to the left, and result in greater suction generated at the pump inlet. In addition, as will be described in reference to clamp 25 shown in FIG. 2a, 2b and FIG. 4, the present invention provides the user with some control over the degree of inlet suction generated by the suction pump.

It should also be obvious that shunt 124 could be placed anywhere between pump inlet and pump outlet, for example, as shown in FIG. 1 by the dashed outline of connectors 123 and 126 and shunt 124 placed near the inlet of reservoir 14 and denoted as 123', 126' and 124' respectively.

A similar circuit as described for the suction pump can be used for emptying blood from one of the heart chambers. For illustration only and not as a limitation to the scope of the invention, the left ventricle (LV) is chosen as the chamber to be emptied. As illustrated in FIG. 1 and, in more detail in FIG. 2a, tubing 18 is connected at one end to LV catheter (not shown) and used to withdraw blood from the LV (not shown) of a patient undergoing cardiac surgery. Tubing 18 usually has a ¼" ID and is usually connected to tubing 29 via a ¼" by ¼" polycarbonate perfusion connector (e.g. part # EC-2125, Gish Biomedical, Santa Ana, Calif. 92705 not shown), said connection usually made by the user at 29a. The connector usually delineates the sterile patient field and the heart-lung machine. The connections can also be made as described for the connection between tube 1 and 2. Means to connect tube 18 to 29 usually done by the user, can also be provided by solvent bonding tube 29 at 29a to one open end of standard rigid PVC connector 33, said connector accepting ¼" ID tube at its other open end. The outlet of tube 18 forms fluid communication with the inlet of unidirectional valve 28 via tube 29. For the purposes to be described hereinafter, valve 28 preferably has minimal resistance to flow and is preferably transparent (e.g. model PP/7 made by Haemotronic of Mirandola, Modena, Italy). The outlet of valve 28 connects to tube 27 at 27b forming fluid communication to the inlet of pump tubing 230 and shunt tubing 24 via three way connector 26. Pump tubing 230 is placed in the raceway of roller pump 13 (LV vent pump) and, if desired, its occlusion set as described by the pump manufacturer. Alternatively, pump 13 can be set in a nonocclusive manner to reduce blood damage and allow another channel between pump inlet and outlet thereby reducing the maximum suction and maximum pressure the pump can generate. The outlet of tube 230 is connected to a second three way connector 23, said three way connector forming fluid communication between the outlet of shunt tubing 24, pump tubing 230 and the inlet of tube 22. Tube 22 provides a fluid path for the patient's blood being withdrawn by roller pump 13 to reservoir 14. Connections to standard cardiotomy reservoirs (e.g. Model # BCR-3500, Baxter/Bentley, Irvine, Calif.) require a ¼" ID flexible tubing. If tube 22 does not have a ¼" ID, then its outlet 22a may be adapted with short ¼" ID flexible tubing 21 and connected, for example, by cyclohexenon at 21b. The blood pumped to reservoir 14 is then returned to the patient in a manner identical to that described in reference to suction pump 4 in FIG. 2b.

To assure that pump 13 does not generate excess suction, the circuit combines the two aforementioned innovations: the properties of pump tubing 230 as placed in pump 13 and shunt tubing 24, said innovations previously described in reference to FIG. 2b for tube 231 placed in suction pump 4 and shunt 124 respectively.

Figure 3A:
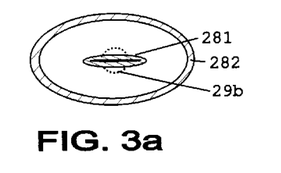
FIG. 3a is a line drawing of valve 28 taken along lines 3 and 3' of FIG. 2 illustrating the radial cross section of said valve in its normally closed state.
Figure 3B:
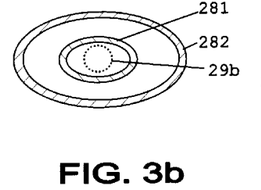
FIG. 3b is a line drawing of valve 28 taken along lines 3 and 3' of FIG. 2 illustrating the radial cross section of said valve in its open state.

If pump 13 is accidentally reversed, the heart may become over distended with blood, or air in the line may be pumped into the patient. Such an accident can be prevented by unitary valve 28. This valve, better shown in FIG. 3a–f, allows flow from the patient to reservoir 14 through flat thin tube 281, said thin tube 281 forming fluid communication at its inlet to tube 29 at 29b and to housing 282 at its outlet. In its natural state thin section 281 is flat as shown in FIG. 3a. When liquid flows from tube 29 to tube 27 via valve 28, thin tube 281 opens as shown in FIG. 3b. Should the pump direction be reversed, the outlet of section 281 collapses (FIG. 3b), stopping unintended flow from reaching the patient. Overpressurization of tube 27 and housing 282 is prevented by the pumped fluid shunting from connector 26 to connector 23 mostly via shunt tube 24 and to some extent through the gap of the nonocclusive pump tube 230. Thus, reversal of flow is contained within the extracorporeal circuit, unlike prior art devices where pump reversal results in blood "spitting" out of the extracorporeal circuit and exposing the user and patient to dangerous contamination.

The open fluid communication between pump inlet and outlet provided by shunt 24 affords another innovative advantage lacking in prior art devices: should pump 13 fail or stopped by the user, the shunt allows the blood from the LV to flow to reservoir 14 by gravity. It should be obvious that should the pump stop, the flow is limited by the resistance of the shunt and the height difference between reservoir 14 and the LV (patient). Either way, the present invention provides a direct fluid communication between patient and cardiotomy reservoir, whereas prior art devices do not.

The present invention also allows the user control over the maximum suction generated by the roller pump. Should suction greater than that possible with an open shunt be desired, shunt 124 with pump 4 or shunt 24 with pump 13 (shown in FIG. 2b and 2a respectively), can be partially or fully clamped off. To assure proper shunt clamping and unclamping, the tube used for the shunt should be soft yet sufficiently resilient to return to its normal shape when unclamped, thereby rendering shunt resistance unchanged, such as provided by silicone, polyvinyl chloride or polyurethane tubing with a Shore hardness of 40 A to 80 A. To facilitate shunt clamping the present invention may also incorporate the well-known tube clamp 25 (e.g. model E/3 made by Haemotronic of Mirandola, Modena, Italy) shown as an outline in FIG. 2a and 2b and in detail in FIG. 4. As shown, shunt tube 24 placed within clamp 25 can be compressed between rigid sections 25f and 25g and maintained compressed by movable hinge 25a latched into locking protrusion 25b, 25c, 25d or 25e. When latch 25a locks into one of the said protrusions, sections 25f and 25g compress tube 24 thereby reducing the effective cross sectional area of shunt 24, increasing resistance to shunt flow and therefore increasing the maximum suction possible at the inlet to pump 13. Latching hinge 25a to protrusion 25e compresses tube 24 completely closed. Latching hinge 25a to protrusion 25c or 25d results in a resistance increase intermediary to that of 25b and 25e. A similar clamp can be placed over shunt tube 124 to affect the degree of suction generated by pump 4.

TABLE 2

Typical inlet pressure (mmHg) with prior art devices and present invention.

| Device | Type |
|---|---|
| Standard tube | none |
| Quest | valve |
| RLV-2100B | valve |
| Bard | valve |
| Sarns | tube collapse |
| Better-Venter ™ | shunt |

Figure 6C:
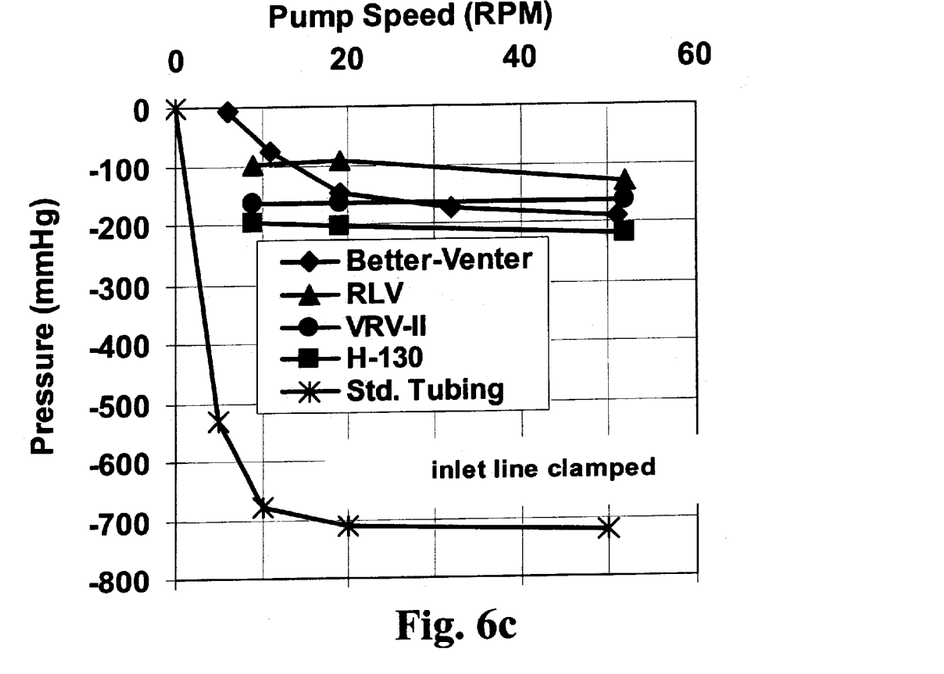
FIG. 6c shows pump inlet pressure as a function of speed with the pump inlet tubing clamp off.

A study was conducted comparing the suction generated at the pump inlet with standard tubing and prior art devices to one preferred embodiment of the present invention. Inlet pressure was monitored and recorded at different pump (6" raceway made by Stockert now a Div. of Sorin Biomedical, Irvine, Calif.) speed as the pump inlet tubing was clamped off. The results are summarized in FIG. 6c. It is clear that the present invention (labeled Better-Venter™) limited pump inlet pressure as well as provide control over the suction generated. Here the control (from 0 to −200 mmHg) was obtained by adjusting pump speed. By contrast, with prior art devices, pump inlet pressure was practically unchanged over the entire range of pump speeds tested.

Figure 6D:
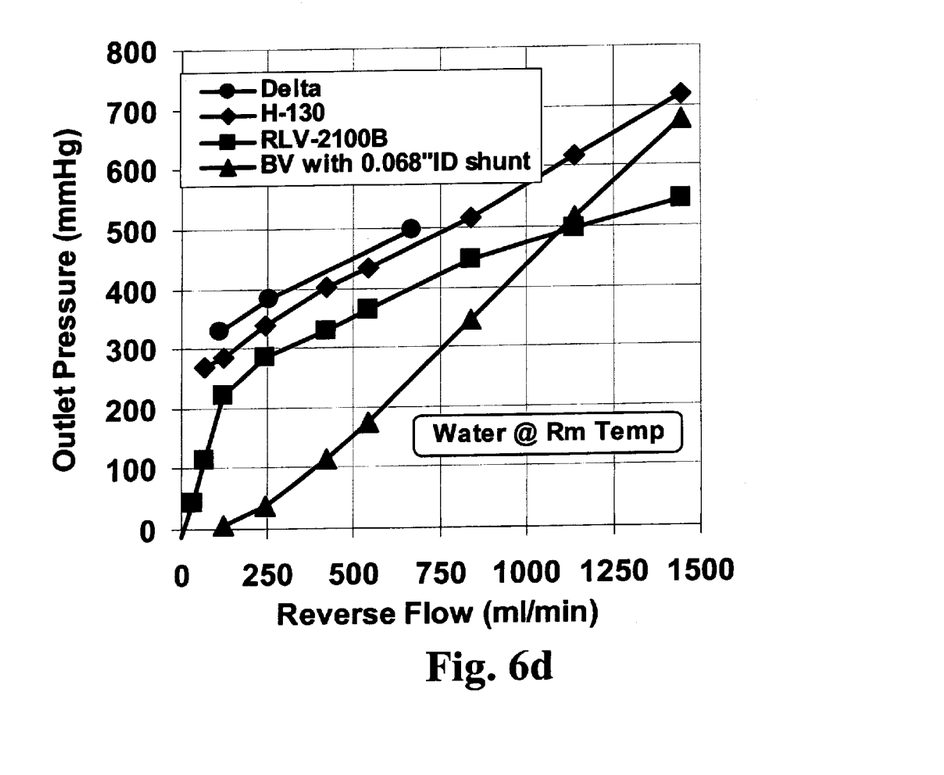
FIG. 6d shows the positive pressure generated at the pump inlet when accidental pump reversal was simulated.

In another test, the conditions of accidental pump reversal was simulated and he resulting positive pressure generated at the pump inlet was recorded, see FIG. 6d. Clearly, the present invention limits the pressure at the pump inlet to levels that prevent blowouts. It should be obvious that lower pressure can be obtained by increasing the internal diameter (ID) of the shunt.

Figure 5A:
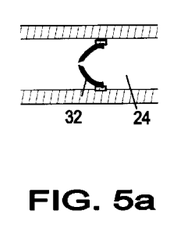
FIG. 5a is a schematic representation of a bi-directional pre-loaded pressure valve that can be placed in line with the shunt illustrated in FIG. 2.
Figure 5B:
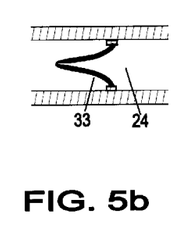
FIG. 5b is a schematic representation of a unidirectional pre-loaded pressure valve that can be placed in line with the shunt illustrated in FIG. 2.
Figure 5C:
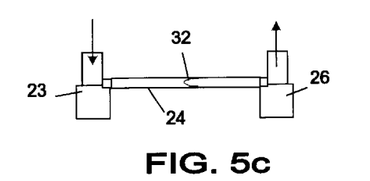

FIG. 5c is a schematic representation of another preferred embodiment of the present invention incorporating a preloaded bidirectional pressure valve 32, also shown in FIG. 5a, in shunt 24 or 124 illustrated in FIG. 2a and 2b respectively. The preload pressure on valve 32 for flow from pump outlet to inlet can be adjusted such that valve 32 opens whenever the pressure difference across it reaches a critical level, said level dependent on the allowed suction at the inlet of pump 13 or 4. Preferably, such preload would open the valve when pump flow from pump tubing (230 or 231) before pump flow drops below 50% of rated flow. This assures that tube 230 or 231 does not collapse to a degree that results in its opposite walls contacting, a condition that may result in additional blood damage. The preload on the valve for flow from pump inlet to outlet (which can occur during the aforementioned accidental pump reversal or pump stoppage) preferably should be minimized. Preloaded valve 32 thereby limits the suction at the inlet of pump 13 or 4, much like prior art devices except that it directs blood from the pump outlet to the pump inlet without introducing air into the blood stream. Similarly, accidental pump reversal results in blood pumped from pump inlet to outlet thereby containing the blood within the blood circuit rather than splattering it across the room as prior art devices may do. It should be obvious that when preloaded valve 32 is used to control the suction the aforementioned resistance to flow through shunt 24 or 124, is not required, said shunts have a larger ID, preferably accommodating valve 32 as shown in FIG. 5c. Preloaded valve 32 can be, for example, the type described in U.S. Pat. No. 4,341,239 (Vernay Laboratories, Yellow Spring Ohio).

Another embodiment of the present inventions uses the combination of preloaded bi-directional pressure valve 32 and pump tubing 231 or 230 having the flow characteristics of standard tubing (e.g., Tygon S-50-HL PVC, shore hardness 65 A and/or ID/wall<5).

In another embodiment of the present inventions, where a flow reversal is not a concern, a preloaded unidirectional pressure valve 33 can be used in place of bi-directional valve 32. One example of a valve 33 is a preloaded duckbill valve.

Another innovation of the present invention is the visual means alerting the user to excess inlet suction provided by changes in shape and/or color of valve 28 as illustrated in FIG. 3. FIGS. 3a–d are a cross section view of valve 28 taken along line 3 and 3' shown in FIG. 2a. In each of said Figures, item 281 is the collapsible thin soft flat channel that allows flow in one direction and is in fluid communication with tube 29 at inlet 29b also shown in FIG. 2a. Item 282 is the housing surrounding thin section 281 that provides fluid communication between flat channel 281 and outlet tube 27 when said valve is closed. FIG. 3d illustrates one preferred embodiment of the same cross section showing an open valve under a condition of excess pump inlet suction (e.g., <−300 mmHg). Under said excess suction condition, housing 282 tends to collapse such that its cross section is a flattened ellipse, and under extreme suction conditions a FIG. 8 shape shown in FIG. 3d and seen by the user as a collapsed state as shown in FIG. 3f. In fact, under extreme conditions the opposite walls of housing 282 collapse to such a degree as to touch resulting in absence of blood in the area of wall contact. This is visualized as a color change (from red to clear) appearing in the mid section of valve 28 as shown in FIG. 3e. Thus, a shape change and, in the extreme, a color change in valve 28 indicates excess suction in the present invention. The suction required to effect these changes can be designed with appropriate choice of material, hardness and wall thickness, the latter affecting the aforementioned ID/wall of housing 282. The design criteria that allow valve 28 to collapse at the appropriate negative pressure can be adjusted by the physical properties of the valve housing 282. These properties include the shore hardness of the wall and the ratio of wall thickness to housing diameter. A softer material (lower Shore A) and/or a larger ratio (thinner wall or larger diameter) lower the suction required to cause housing collapse.

Figure 3C:
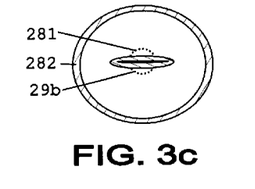
FIG. 3c is a line drawing of valve 28 taken along lines 3 and 3' of FIG. 2 illustrating the radial cross section of said valve when it is closed and its housing is expanded due to excess positive pressure.
Figure 3D:
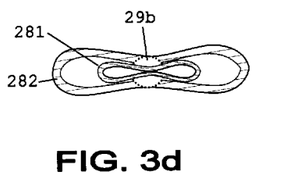
FIG. 3d is a line drawing of valve 28 taken along lines 3 and 3' of FIG. 2 illustrating the radial cross section of said valve when it is almost closed and its housing is collapsed at its midsection due to, and indicating, excess suction.
Figure 3E:
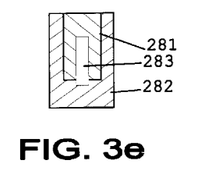
FIG. 3e is front view of valve 28 shown in FIG. 3d illustrating the longitudinal cross section of said valve.
Figure 3F:
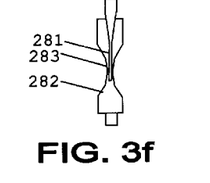
FIG. 3f is a side view of valve 28 shown in FIG. 3e and 3d illustrating the collapsed longitudinal cross section of said valve.

Another innovation of the present invention is the visual means alerting the user to excess inlet pressure due to pump reversal provided by changes in the shape of valve 28. FIG. 3a illustrates the radial cross section of valve 28 taken along lines 3 and 3' shown in FIG. 2 when it is closed due to the pressure at 27b being greater than at 29b, shown in FIG. 2, but not sufficiently greater than atmospheric pressure to cause a shape change in housing 282. This may occur with pump reversal and low speed. Should pump reversal be at high speed, the pressure in housing 282 would be sufficient to expand the housing from an elliptical to a circular cross section, as shown in FIG. 3c, said shape change indicating pump reversal. The design criteria that allow valve 28 to expand at the appropriate positive pressure can be adjusted by the physical properties of the valve housing 282. These properties include the shore hardness of the wall and the ratio of wall thickness to housing diameter. A softer material (lower Shore A) and/or a larger ratio (thinner wall or larger diameter) lower the pressure required to cause housing expansion.

The connections between the various components required to manufacture the invention are either made using solvent bonding, radio frequency (RF) welding, or other similarly useful methods that are appropriate for the integrity of the seal, are cost effective and meet prevailing environmental and manufacturing safety laws.

Figure 8A:
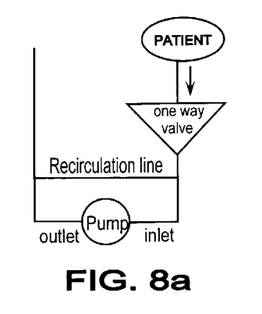
FIG. 8a is a line drawing representing FIG. 1.
Figure 8B:
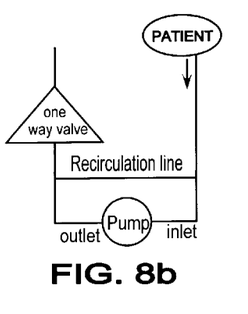
FIG. 8b is a line drawing of another configuration of the present invention with the one way valve placed at the pump outlet and distal to the recirculation line.
Figure 8C:
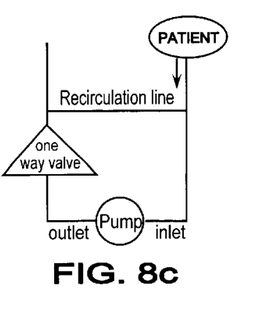
FIG. 8c is a line drawing of yet another configuration of the present invention with the one way valve placed at the pump outlet but proximal to the recirculation line.

FIGS. 8a, b, and c illustrate alternate locations of one way valve 28 described in reference to FIG. 1, 2a, and 3a–f. FIG. 8a is a line drawing of the preferred circuit as described in reference to FIG. 2a. FIG. 8b is similar to FIG. 8a except that valve 28 is placed at the outlet of the pump and distal to the recirculation line. FIG. 8c is similar to FIG. 8b except that valve 28 is placed proximal to the recirculation line. In each of these configurations the unidirectional valve prevents back flow to the patient. Both configuration 8b and 8c would and could not generate a high pressure due to accidental pump reversal.

I claim:

1. An improved pump loop for limiting peristaltic pump suction during extracorporeal circulation, said pump loop comprising;
   a first tubing segment for insertion in a roller pump for pumping extracorporeal fluids therethrough, said tubing segment having a pump inlet and a pump outlet and formed of a biocompatible tubing having a shore hardness of less than 80 A and having a first predetermined cross sectional area;
   a second tubing segment shunting said pump inlet and said pump outlet, said second tubing segment creating a resistance to flow between said outlet and said inlet, said second tubing defined by a second cross sectional area that is less than one-tenth the area of the first cross sectional area.

2. An improved pump loop as claimed in claim 1, wherein said loop further comprises a one-way valve in the pump inlet, said one way valve being distal to said second tubing segment.

3. An improved pump loop as claimed in claim 1, wherein said loop further comprises means for adjusting the second cross sectional area of the second tubing segment.

4. An improved pump loop as claimed in claim 3, wherein said means for adjusting the second cross sectional area is an adjustable tubing clamp.

5. An improved pump loop as claimed in claim 3, wherein said means for adjusting the second cross sectional area is an adjustable valve in the second tubing segment.

6. An improved pump loop as claimed in claim 1, wherein said first tubing segment has an inner diameter of 0.20 to 0.50 inches.

7. An improved pump loop as claimed in claim 1, wherein said first tubing segment has an inner diameter of 0.06 to 0.15 inches.

8. An improved pump loop as claimed in claim 1, wherein an inner diameter and said shore hardness of said first tubing segment are matched to an inner diameter of said second tubing segment to shunt greater suction than −300 mmHg from said outlet to said inlet.

9. An improved pump loop as claimed in claim 8, wherein said first tubing segment begins to collapse at suction greater than 200 mmHg at said pump inlet.

10. An improved pump loop as claimed in claim 1, wherein said first tubing segment has an inner diameter of 0.20 to 0.50 inches.

11. An improved pump loop for a roller pump for limiting peristaltic pump suction during venting a myocardium, said pump loop comprising;

a first tubing segment for insertion in a roller pump for venting the myocardium at a first defined flow rate, said tubing segment having a pump inlet and a pump outlet and formed of a biocompatible tubing having a shore hardness of less than 80 A that causes partial collapse of said first tubing segment when an impeded flow at said inlet is less than 30% of said defined flow rate;

a second tubing segment shunting said pump inlet and said pump outlet, said second tubing segment limiting excess negative pressure at said pump inlet by providing a second pump flow rate form said outlet to said inlet, said second pump flow rate providing at least 20% of the first defmed flow rate.

12. An improved pump loop as claimed in claim 10, wherein said loop further comprises a one-way valve between the myocardium and said pump inlet, said one way valve being distal to said second tubing segment.

13. An improved pump loop as claimed in claim 10, wherein said loop further comprises means for adjusting the second pump flow rate through the second tubing segment.

14. An improved pump loop as claimed in claim 13, wherein said means for adjusting the second pump flow rate is an adjustable tubing clamp.

15. An improved pump loop as claimed in claim 14, wherein said means for adjusting the second pump flow rate is an adjustable valve in the second tubing segment.

16. An improved pump loop as claimed in claim 10, wherein said second tubing segment has an inner diameter of 0.06 to 0.15 inches.

17. An improved pump loop as claimed in claim 10, wherein an inner diameter and said shore hardness of said first tubing segment are matched to an inner diameter of said second tubing segment to shunt greater suction than −300 mmHg from said outlet to said inlet.

18. An improved pump loop as claimed in claim 17, wherein said first tubing segment begins to collapse at suction greater than 200 mmHg at said pump inlet.

19. An improved pump loop as claimed in claim 10, wherein said pump loop further comprises a visual indicator at said pump inlet in indicate negative pressure at said pump inlet.

20. An improved pump loop as claimed in claim 10, wherein said pump loop further comprises first and second three way connectors, with said first three way connector connecting said pump inlet, said first tubing segment and said second tubing segment, and said second three way connector connects said pump outlet, said first tubing segment and said second tubing segment.

* * * * *